United States Patent
Meldrum

(10) Patent No.: US 12,293,829 B2
(45) Date of Patent: May 6, 2025

(54) SYSTEM AND METHOD FOR VESTIBULAR AND/OR BALANCE REHABILITATION

(71) Applicants: THE PROVOST, FELLOWS, SCHOLARS AND OTHER MEMBERS OF BOARD OF TRINITY COLLEGE DUBLIN, Dublin (IE); Royal College of Surgeons in Ireland, Dublin (IE)

(72) Inventor: Dara Meldrum, Dun Laoghaire (IE)

(73) Assignee: The Provost, Fellows, Foundation Scholars and the other members of Board, of the College of the Holy, Dublin (IE)

( * ) Notice: Subject to any disclaimer, the term of this patent is extended or adjusted under 35 U.S.C. 154(b) by 0 days.

(21) Appl. No.: 18/268,708

(22) PCT Filed: Dec. 24, 2021

(86) PCT No.: PCT/EP2021/087649
§ 371 (c)(1),
(2) Date: Jun. 21, 2023

(87) PCT Pub. No.: WO2022/136706
PCT Pub. Date: Jun. 30, 2022

(65) Prior Publication Data
US 2024/0055117 A1     Feb. 15, 2024

(30) Foreign Application Priority Data
Dec. 24, 2020    (EP) .................................. 20217272

(51) Int. Cl.
*G16H 40/67*    (2018.01)
*A61B 5/00*    (2006.01)
(Continued)

(52) U.S. Cl.
CPC ........... *G16H 40/67* (2018.01); *A61B 5/7405* (2013.01); *A61B 5/742* (2013.01); *A61B 5/7475* (2013.01); *G06F 3/012* (2013.01); *G16H 20/30* (2018.01)

(58) Field of Classification Search
CPC ........ G16H 40/67; G16H 10/60; G16H 20/70; G16H 40/63; G16H 20/30; G06F 3/012;
(Continued)

(56) References Cited

U.S. PATENT DOCUMENTS 9,526,946 B1 * 12/2016 Zets .................... G09B 19/0038
10,342,473 B1    7/2019 Berme et al.
(Continued)

FOREIGN PATENT DOCUMENTS

WO    2015/048839    4/2015

OTHER PUBLICATIONS

International Search Report issued in PCT/EP2021/087649 on Apr. 13, 2022 (21 pages).

*Primary Examiner* — Jack Yip
(74) *Attorney, Agent, or Firm* — ARC IP Law, PC; Joseph J. Mayo

(57) ABSTRACT

A system and method for vestibular and/or balance rehabilitation by monitoring and measuring head motion data of a user having vestibular impairment. The system as includes a user device, a head tracking device, and a remote server device. The user device receives therapeutical configuration data prescribed by a therapist using the remote server device. A visual and auditory and/or haptic stimuli is generated in the user interface according to the received therapeutic configuration data during a training session or initial assessment session. Head motion data from the head tracking device during the training session is received along with user inputted data pertaining to symptoms of the user. The remote
(Continued)

server device receives and processes the head motion and positional data, the user inputted symptoms data and communicates a set of updated therapeutic configuration data to the user device based on the processed data for use in a next training session.

10 Claims, 6 Drawing Sheets

(51) Int. Cl.
*G06F 3/01* (2006.01)
*G16H 20/30* (2018.01)

(58) Field of Classification Search
CPC ..... A61B 5/486; A61B 5/6803; A61B 5/6814; A61B 2505/09; A61B 5/7405; A61B 5/742; A61B 5/7475; A61B 5/0022; A61B 5/1114; A61B 5/1122; A61B 5/1104; A61B 5/4023
See application file for complete search history.

(56) References Cited

U.S. PATENT DOCUMENTS

| 10,736,545 | B1 | 8/2020 | Berme et al. |
| 2009/0240172 | A1* | 9/2009 | Fernandez Tournier ................... A63B 26/003 600/595 |
| 2010/0306701 | A1* | 12/2010 | Glen ....................... G06Q 10/00 715/810 |
| 2016/0262608 | A1 | 9/2016 | Krueger |
| 2018/0317837 | A1* | 11/2018 | Burwinkel ........... H04R 25/554 |
| 2020/0138364 | A1 | 5/2020 | Fabry et al. |
| 2020/0143703 | A1* | 5/2020 | Fabry .................. A61B 5/7405 |
| 2020/0330775 | A1* | 10/2020 | Unterweissacher . A61B 5/1121 |

\* cited by examiner

SYSTEM AND METHOD FOR VESTIBULAR AND/OR BALANCE REHABILITATION

FIELD

The present disclosure relates to a system and method for vestibular and/or balance rehabilitation, and more particularly to a system and method for vestibular rehabilitation based on real time head motion data.

BACKGROUND

It is estimated that thirty five percent (35%) of adults have balance impairment, and that dizziness and vertigo are prevalent in twenty percent (20%) of adults. A combination of both results in about twelve-fold risk of falling which is associated with high morbidity and significant mortality. It is further estimated that across jurisdictions such as Europe and the United States between 53 and 95 million individuals have vestibular loss In about eighty percent (80%) of cases, a medical professional is consulted and in about eighty percent (80%) of cases at least one recurrence is experienced.

Dizziness and imbalance can be rehabilitated effectively by physical exercise with a specialised form of treatment known as vestibular rehabilitation. Vestibular rehabilitation is a form of therapy that is effective in reducing the unpleasant symptoms of dizziness and vertigo, and in improving gaze stability, balance, gait, and the general quality of life in patients with vestibular impairment.

At present, access to this treatment and expert capacity is low leading to an impaired population that is under-served. During vestibular rehabilitation, therapists prescribe home exercises for patients. Most conventionally known methods for vestibular rehabilitation are pen and paper based; and implementing and successfully completing a home exercise programme is currently problematic, time consuming for therapists, and difficult for patients to get right due to the lack of supervision. Patients very often stop exercising until their next clinic visit if the prescribed sets of exercises make them feel nauseated or dizzy, and this may in turn lead to loss of valuable time. Paper based prescription of home exercises inhibit the patient's ability to remember the correct manner of performing them, and patients also find it difficult to adhere to prescribed timelines. Further, lack of opportunity to regularly supervise performance of exercises limits a therapist's ability to successfully treat patients and to provide effective feedback. There is also no scope for remote interaction of patients and therapists in case of paper-based methods.

Devices which deliver video prescriptions without sensing patient responses are also known in the art. However, most of the drawbacks associated with paper based methods are attributable to such devices as well, since they offer no means for patients and therapists to exchange feedback or to track in real time the manner in which the exercises are being performed.

European patent publication number EP 3257435 A1 discloses an apparatus and method for vestibular impairment by sensing eye movements using a head mounted virtual reality visual display system. Treatment of vestibular impairment by tracking eye movements is generally not cost effective. US patent publication numbers US2020/138364, Fabry et al, and U.S. Pat. No. 10,736,545, Berme et al, discloses a hearing assistive device and method for providing visual feedback to a subject undergoing physical therapy or vestibular movement training. The system is complex and does not provide sufficient feedback to either the user or a clinician to effectively monitor a physical therapy or vestibular movement training programme. For example, the subjective symptoms of vertigo and imbalance are of prime importance and a source of great distress to patients with vestibular impairment. No system to date measures what the actual user is experiencing during or after a training programme and uses this information to inform the clinician/patient of progress.

There is therefore an unresolved and unfulfilled need for a system and method for vestibular rehabilitation, and that which enables regular supervision of patients and exchange of feedback, and this forms the primary objective of the present invention.

SUMMARY OF INVENTION

The present invention relates to a system and method for vestibular and/or balance rehabilitation based on real time head motion data, as set out in the appended claims.

In a preferred embodiment of the present invention, a system for vestibular rehabilitation is provided. The system comprises at least one user device, a remote server device, and at least one head tracking device. The user device has a data processing and networking means, and a display means, and is operably interfaced with each head tracking device and the remote server device. The remote server device has a data processing and networking means and display means is operably interfaced with each user device. Each head tracking device is adapted to capture head motion data of a user in real time.

In an embodiment of the present invention, the captured head motion data includes amplitude of head motion, frequency and speed of head motion, angular velocity and the head motion device comprises an accelerometer, a gyroscope, and a magnetometer.

The head motion of the user is in response to personalised exercises or personalised therapeutic configuration data prescribed by a therapist. The exercises are prescribed based on clinical diagnosis of the user and is communicated through the remote server device to each user device. Each user device is configured to receive the prescribed exercises from the remote server device, output a user interface to the display means, and generate a visual and audible stimulus to each user based on the received exercises. The head motion data of the user in response to the visual and audible stimuli is measured by the head tracking device and is communicated in real time to the corresponding user device, thereby providing real-time corrective feedback on the accuracy of the head movement in relation to the head motion prescribed by the therapist. In an embodiment of the present invention, head motion data is communicated to the user device through a Bluetooth Low Energy Scanner.

In one embodiment a haptic stimulus is generated. For example, the haptic stimulus is in the form of a vibrating device or any suitable device capable of delivering a haptic stimulus to the user.

The user device is further configured to generate real time visual feedback to the user in the display means according to the received head motion data. Such real time visual feedback to the user includes for example, velocity, movement plane and frequency of head movement and how much time is left in a training session. Feedback that can be displayed on the user device after the training session includes percentage completed and symptoms. Other feedback which can be communicated to the server can display—percentage of training completed, duration of exercise performance/training, symptom rating, also in response to training. Symptom data perceived by the patient, (instances of dizziness, nausea, anxiety, imbalance and oscillopsia) can be inputted at the user device side. The user device communicates the head motion data and symptom data to the remote server device, and if needed, the therapist monitoring the remote server device communicates to the user device, a set of updated exercises based on the received feedback and head motion data.

In an embodiment of the present invention, the user interface of the user device is adapted to provide a symptoms screen which allows users to input symptoms, for example their level of dizziness/vertigo/nausea/pain/headache before and after exercises. The user interface is further adapted to provide a progress screen allowing patients to review progress of their exercise programme, and a reading screen to access personalised educational material prescribed to a user.

In a preferred embodiment of the present invention a method for vestibular rehabilitation is provided. The method comprises the first step of displaying a visual stimulus to a user having vestibular impairment, wherein said visual stimulus corresponds to a set of exercises or therapeutic configuration data representative of the clinical diagnosis of the user. The real time head motion of the user, in response to the generated visual stimulus, is measured and monitored in real time. Based on the measured head motion data, a visual feedback is generated to the user. Further, according to the measured head data and the visual feedback, if the user is experiencing any symptoms such as dizziness/vertigo as a result of performing exercises, an updated set of exercises can be generated.

In one embodiment the auditory stimuli comprises a metronome beat wherein the frequency of the metronome beat can be adjusted based on the head motion data.

The present invention enables real time and remote tracking and supervision of vestibular rehabilitation by therapists. Electronic registration of symptom burden of exercises for patients, that is, monitoring responses to exercise and measuring any increase or decrease of symptoms, enables therapists to update exercises based on the data received from the user device by the remote server device and the needs and requirements of patients. The ability to remotely interact with the therapist gives greater confidence to patients and enables the provision of effective adjustments to training/exercise prescription/therapy f. Real time tracking and measurement of head motion data while performing exercises ensures greater reliability and accuracy for treatment of vestibular impairment.

In another embodiment of the invention there is provided a system and method for for the treatment of vestibular impairment, comprising at least one user device having data processing and networking means and a display; at least one head tracking device adapted to monitor head motion in real time and operably interfaced with the user device; and a remote server device having data processing and networking means and display means, and operably interfaced with the or each user device; the or each personal computing device is configured to: receive therapeutic configuration data from the remote server, representative of a clinical diagnosis of the device user; output a user interface on the display; generate visual stimulus in the user interface according the received therapeutic configuration data; receive head motion data from the head tracking device during the user's exposition to the stimulus; and generate visual feedback in the user interface according the received head motion data.

In one embodiment there is provided a system for vestibular and/or balance rehabilitation, the system comprising:
at least one user device having a data processing and networking means, and a display means;
at least one head tracking device adapted to measure head motion data in real time and operably interfaced with the user device; and
a remote server device having data processing and networking means and an optional server display means, and operably interfaced with the, or each, user device;
characterised in that the, or each, user device is configured to:
receive therapeutic configuration data from the remote server device representative of a clinical diagnosis specific to a device user;
output a user interface on the display means;
generate visual and auditory stimuli in the user interface according to the received therapeutic configuration data during a training session, wherein the auditory stimuli comprises a metronome beat such that the frequency of the metronome beat is configured to be adjustable based on the therapeutic configuration data;
receive head motion data from the, or each, head tracking device during the training session;
receive user inputted data pertaining to one or more symptoms of the user; and
generate real time sensory feedback in the user interface according to the received head motion data, and
wherein the remote server device is configured to receive and process the head motion and positional data and the user inputted symptoms data and communicate a set of updated therapeutic configuration data to the user device based on the processed data for use in a next training session.

In one embodiment there is provided a system for vestibular and/or balance rehabilitation, the system comprising:
at least one user device having data processing and networking means, and a display means;
at least one head tracking device adapted to measure head motion data in real time and operably interfaced with the user device;
wherein the, or each, user device is configured to:
receive therapeutic configuration data representative of a clinical diagnosis specific to a device user;
output a user interface on the display means;
generate a visual and auditory stimuli in the user interface according to the received therapeutic configuration data during a training session, wherein the auditory stimuli comprises a metronome beat such that the frequency of the metronome beat is configured to be adjustable based on the therapeutic configuration data;
receive head motion data from the head tracking device during the training session;
receive user inputted data pertaining to one or more symptoms of the user; and
generate real time visual feedback in the user interface according to the received head motion data; and
process the head motion and positional data and, the user inputted symptom data and update a set of updated therapeutic configuration data to the user device based on the processed data for use in a next training session.

There is also provided a computer program comprising program instructions for causing a computer program to carry out the above method which may be embodied on a record medium, carrier signal or read-only memory.

The present invention hence provides a cost effective and robust solution to problems identified in the art. Other advantages and additional novel features of the present invention will become apparent from the subsequent detailed description.

BRIEF DESCRIPTION OF DRAWINGS

The invention will be more clearly understood from the following description of an embodiment thereof, given by way of example only, with reference to the accompanying drawings, in which:—

DETAILED DESCRIPTION OF DRAWINGS

Figure 1:
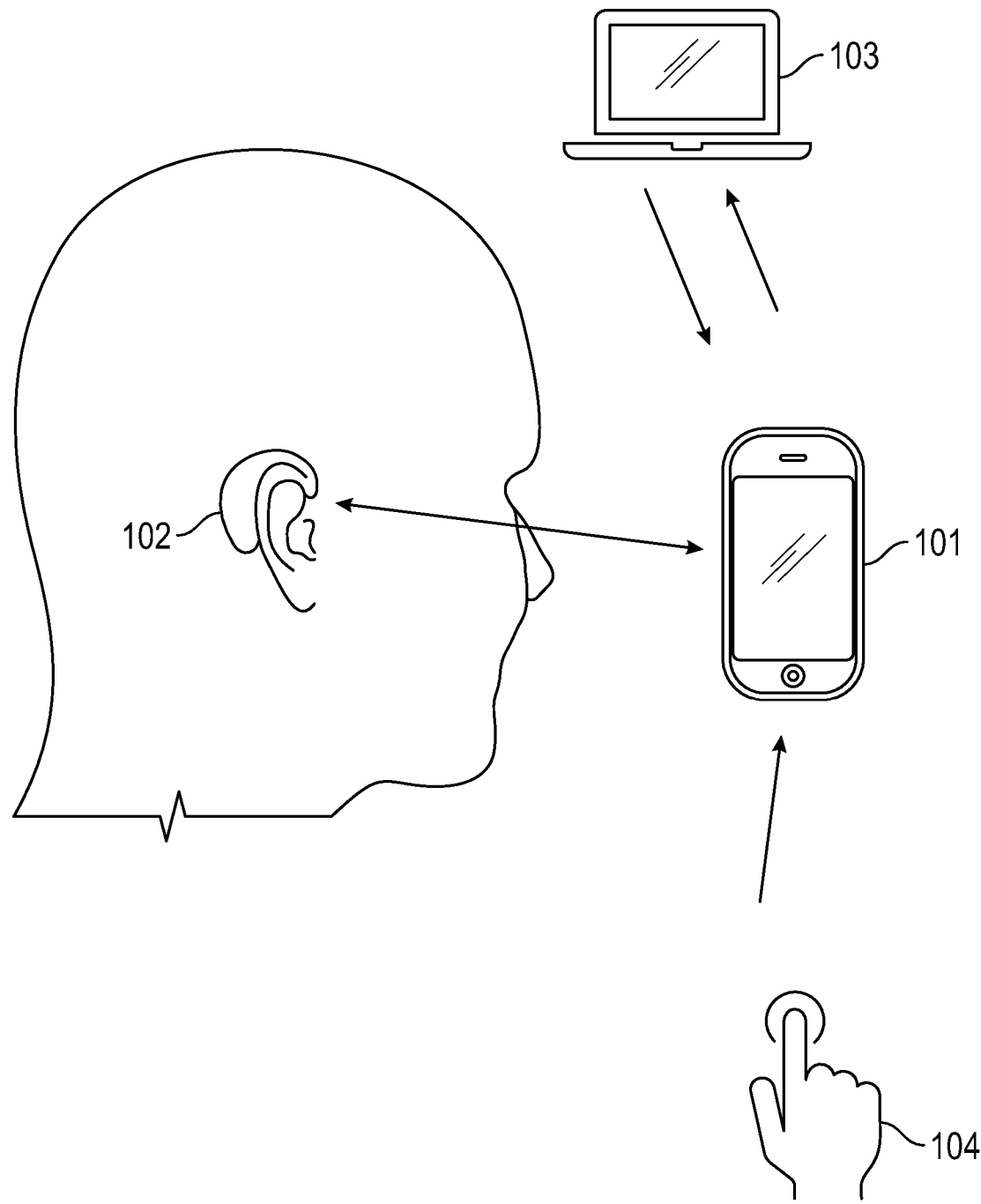
FIG. 1 is a schematic diagram of a system illustrating a preferred embodiment of the present invention.

FIG. 1 illustrates a system as per a preferred embodiment of the present invention. The system comprises at least one user device 101, a remote server device, and a head tracking device 102. Each user device 101 and the remote server device 103 have a data processing and networking means. The user device 101 has a non-transitory memory means operably interfaced to it. The user device 101 and the remote server device 103 may be for example, a personal computer, a portable device such as a tablet computer, a laptop, a smart phone, a connected household device or any operating system based portable device or any cloud hosted enterprise business rule engine. The operating system deployed on the user device and the remote server device may be Windows, OSX, Linux, iOS, Android, or the like. The memory means may be any internal or external device or web-based data storage mechanism adapted to store data.

Each user device 101 is operably interfaced with the head tracking device 102 and the remote server device 103, and further comprises a display means or screen. The remote server device 103 is operably interfaced with the user device 101 and is configured to enable a therapist or clinician to communicate personalized therapeutic configuration data to a user of each user device 101. The user device 101 is configured to receive therapeutic configuration data from the remote server device 103. This therapeutic configuration data can be generated based on an initial assessment of the user performed by a clinician or a therapist before a first training session. The remote server device 103 is configured to process received data from the user device 101. All data received from the user device 101 and head sensor 102 can be triangulated, analysed and graphically represented. The therapeutic configuration data communicated to each user device 101 corresponds to, and is representative of, the clinical diagnosis specific to each user. The head tracking device 102 is operably interfaced with each user device 101 and is adapted to measure head motion data of the user in real time. The head motion of the user is in response to a visual and/or audio stimulus generated based on the therapeutic configuration data received by the user device 101. It will be appreciated that a haptic stimulus can also be provided. The visual and/or audio stimulus is generated in a user interface of the display means of the user device 101 and is viewed by the user. An important feature of the system is that the user can input 104 various metrics that are used to help generate personalised therapeutic configuration data. The metrics are specific to the user, and can include symptoms the user is feeling, goals that the user would like to achieve, problems the user is feeling and medication usage and the like or other relevant metrics.

In an embodiment of the present invention as shown in FIG. 1, the head tracking device 102 is designed to be capable of being worn behind the ear of the user. The head tracking device 102 comprises a plurality of data sensors such as for example, an accelerometer, a gyro-meter, and a magnetometer. The head tracking device 102 applies sensor fusion processing to produce real time metrics of head motion data such as for example, frequency of pitch and yaw rotations, average centroid angle of each head swing, amplitude of head motion, and speed of head motion. The head tracking device 102 communicates the real time head motion data of the user to the user device through standard communication protocols, such as Bluetooth Low Energy or the like. The user device 101 is configured to receive the real time head motion data captured by the head tracking device 102. The user device 101 is further configured to generate a real time visual feedback in the user interface of the display means based on the head motion data received from the head tracking device 102. The real time visual feedback provides a confirmation or validation to the user regarding the manner in which the exercises were performed. The system burden of the user while performing head movements is also displayed to the user or the clinician. The system burden can be the level of difficulty a user is experiencing during a training session.

Figure 2A:
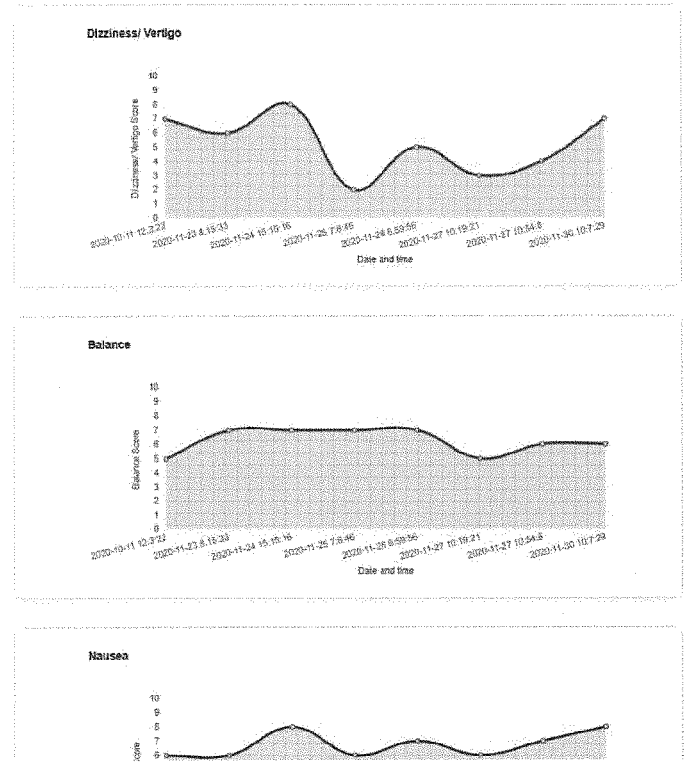
FIGS. 2a, 2b and 2c are example illustrations of the visual feedback generated by a system as per a preferred embodiment of the present invention.
Figure 2B:
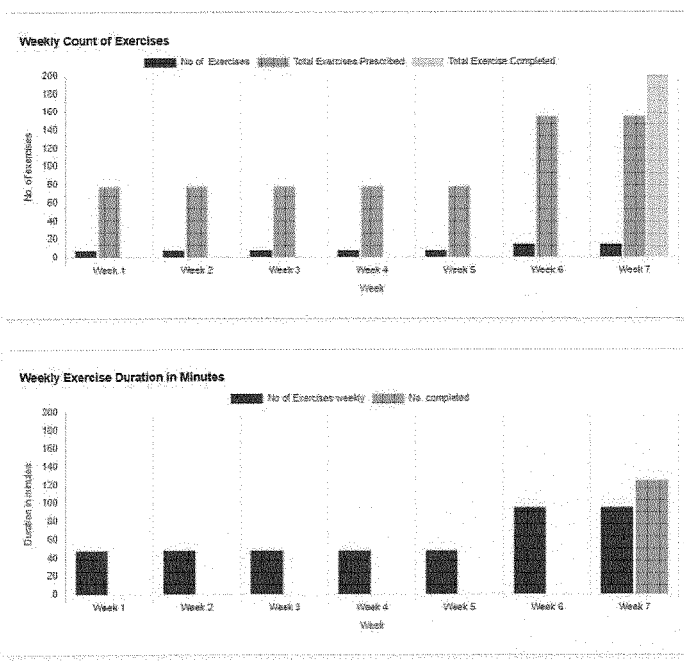
Figure 2C:
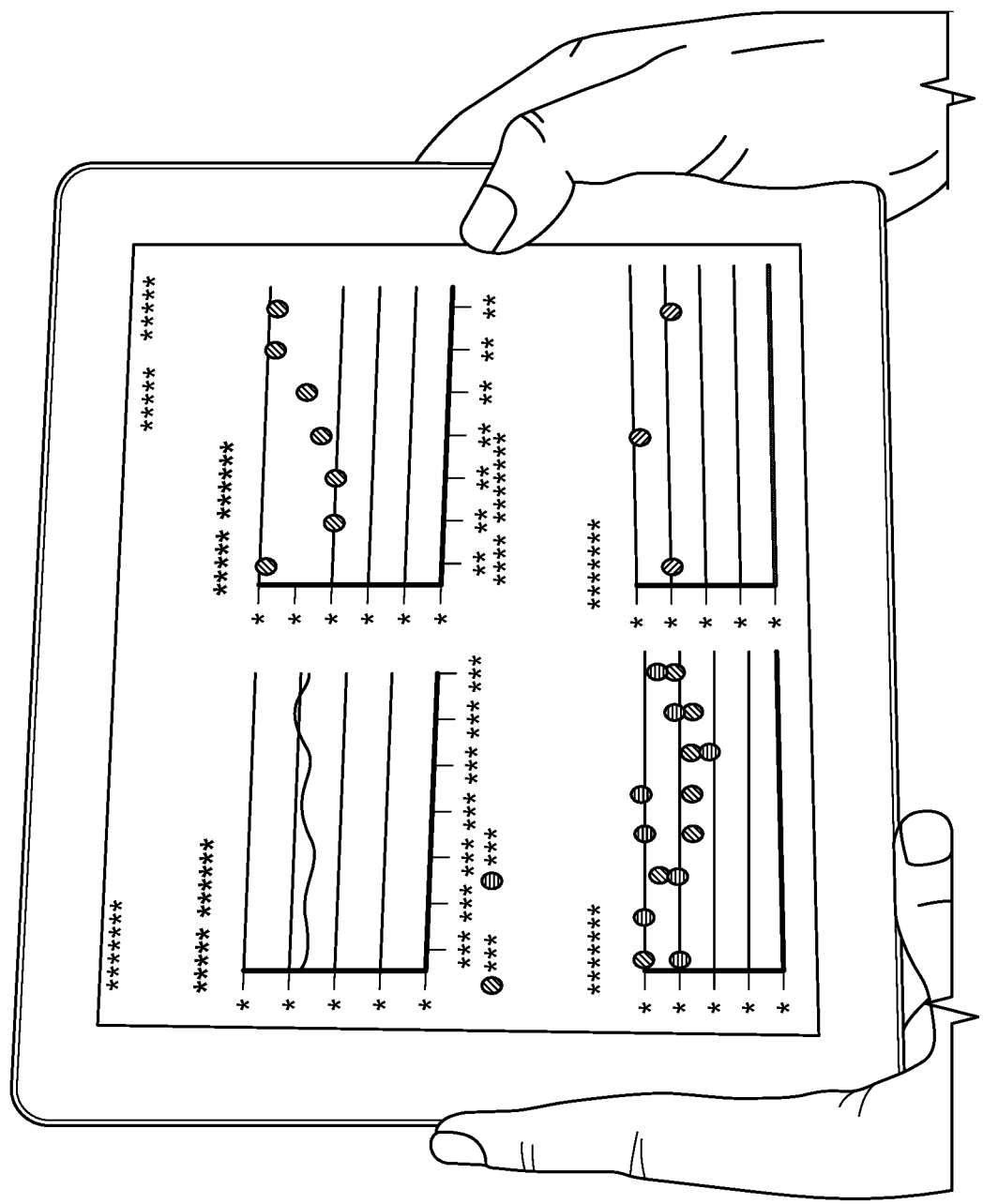

As shown in FIGS. 2a, 2b and 2c, the visual feedback displayed to the user 200, 201, 202 includes for example, the percentage of completion of exercises and user-defined goals, NRS rating scale indicating symptoms of dizziness, vertigo, imbalance, anxiety, nausea, medication usage and oscillopsia experienced by the user. The user device 101 is also configured to communicate the real time head motion data and the symptom data to the remote server device 103. This enables a therapist validating the vestibular rehabilitation session to gain insights regarding the performance levels of the user. Based on these gained insights, if required, the therapist or clinician communicates an updated set of therapeutic configuration data to the user device 101. The updated set of therapeutic configuration data is communicated from the remote server device 103 to the user device 101 to be executed for a next training session. In effect, the remote server device 103 is configured to receive and process the head motion and positional data and real time visual feedback, the user inputted symptoms data. A clinician or therapist can analyse the data and communicate a set of updated therapeutic configuration data to the user device 101 based on the processed data for use in a next training session.

An important aspect of the invention is that the system and method generate real time sensory feedback in the user interface according to the received head motion data. The real time feedback can comprise 1. Correction of direction of movement using text and 2. Correction of speed of movement indicated using colour, text and scale bar. An auditory stimuli can be generated in tandem with the visual feedback, such as a metronome beat, where the frequency of the metronome beat is configured to be adjusted based on the received head motion data and the therapeutic data representative of the clinical diagnosis for the user for a next training session. The real time feedback provided by the system is corrective and can be displayed during the training session to the user on the user device. For example, the corrective feedback can indicate to a user that they are moving too fast or too slow or correct. In addition the corrective feedback can tell the user their head motion is correct or in the wrong direction.

In operation, the auditory stimuli is configured to provide an audio prompting mechanism (an adjustable metronome) to the user that supplements the sensor data which assists the user to perform exercises in addition to the visual prompt (countdown digits on screen) prior to the start of an exercise or training session. The user device 101 provides the prompt, not the head tracking device 102. The audio prompt is based on a prescribed frequency. The frequency can be adjusted between training sessions based on real time performance feedback and generated as frequency and/or velocity performed against what was prescribed and linked to the symptom intensity, i.e. the therapeutic data representative of the clinical diagnosis for the user. The head sensor device 102 not only gives information during vestibular ocular retraining but also can provide feedback during postural stability retraining through parameters of postural sway (velocity, path length and amplitude).

The user device 101 is further adapted to enable users to create templates of frequently used exercises and provides access to educational materials to users which ensures that users gain access to detailed information regarding their clinical condition and their rehabilitation programme. For example, a suite/library of educational material and exercises specific to balance re-education and vestibular rehabilitation, the portfolio provided in video, audio and textual format. The user device 101 is also adapted to provide an interface to users to input their symptoms, for example, the user's level of dizziness/vertigo, while performing exercises, and also provides a progress screen which allows users to review the progress of their rehabilitation programme.

The present invention hence allows exchange of real time feedback between a therapist and a patient. The evaluation of system burden of the user by the therapist ensures optimal management of treatment at home and effective treatment to users suffering from vestibular impairment.

Figure 3:
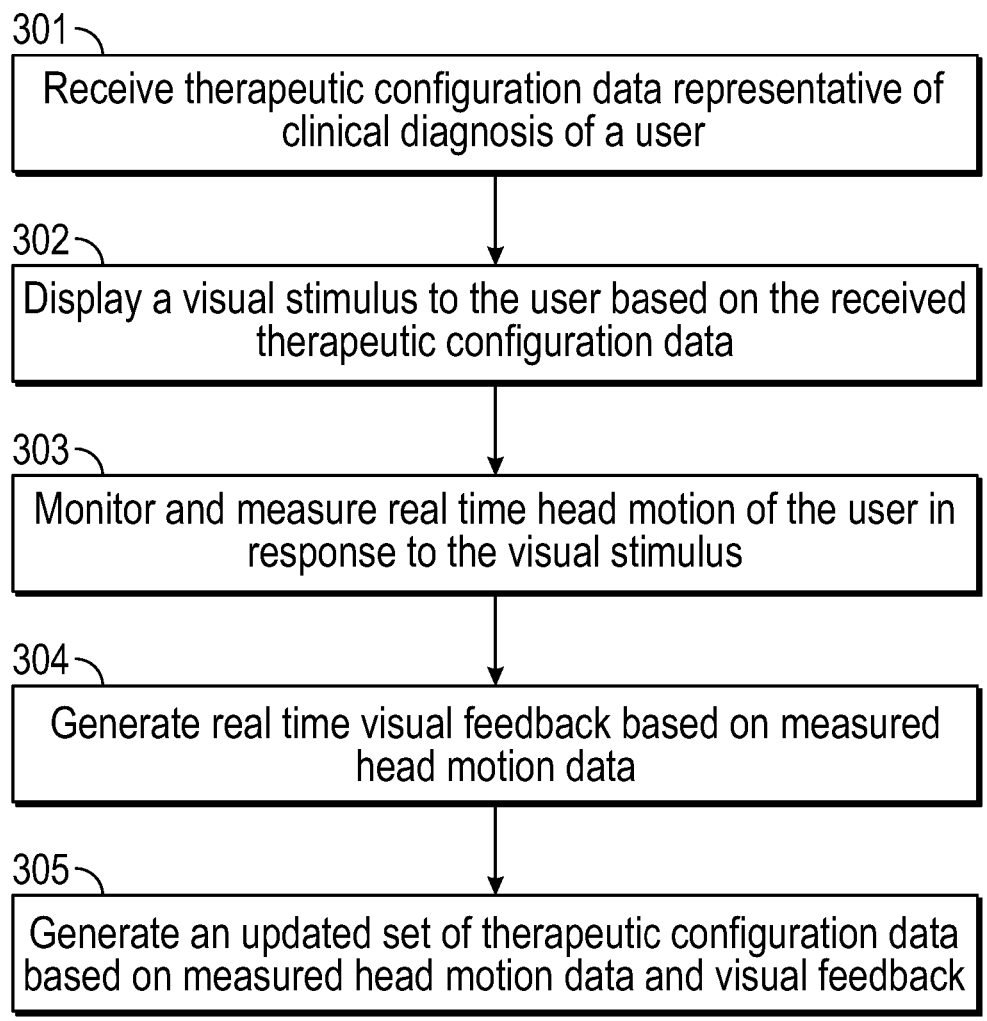
FIG. 3 is a flow diagram illustrating a method as per one aspect of the present invention.

FIG. 3 is a flow diagram illustrating a method as per an embodiment of the present invention. The method comprises the first step of the user device receiving a set of therapeutic configuration data representative of the clinical diagnosis of a user having vestibular impairment 301. Therapeutic configuration data comprises of exercises specifically prescribed for the user by a therapist based on the user's clinical diagnosis. A visual stimulus based on the therapeutic configuration data is further displayed on the user device to the user 302. The visual stimulus, for example, a video graphic is viewed by the user in a user device and enables the user to perform the prescribed exercises. Further, the real time data pertaining to head motion of the user in response to the generated visual stimulus, that is the head motion data while performing exercises based on the displayed video stimulus, is monitored, and measured 303. Such real time data includes for example, the amplitude of head motion and the speed of head motion.

Based on the measured head motion data, a real time visual feedback is generated on the user device to the user 304. Such visual feedback validates adherence of the user to the prescribed exercises, and further provides data points regarding difficulties or symptoms experienced by the user. This includes for example, a metric of pain and rate of perceived exertion experienced by the user while performing exercises. The real time visual feedback and the measured head motion data is also communicated to the therapist on the remote server monitoring the vestibular rehabilitation of the user. In addition symptom data provided by the user to the user device is also communicated to the remote server. Based on the received information and inferences gained from said communication, if deemed required by the therapist, an updated set of therapeutical configuration data can be generated and displayed on the server to the user 305. This is to address scenarios wherein for example, the user experiences excessive symptoms while performing the set of initially prescribed exercises.

Figure 4:
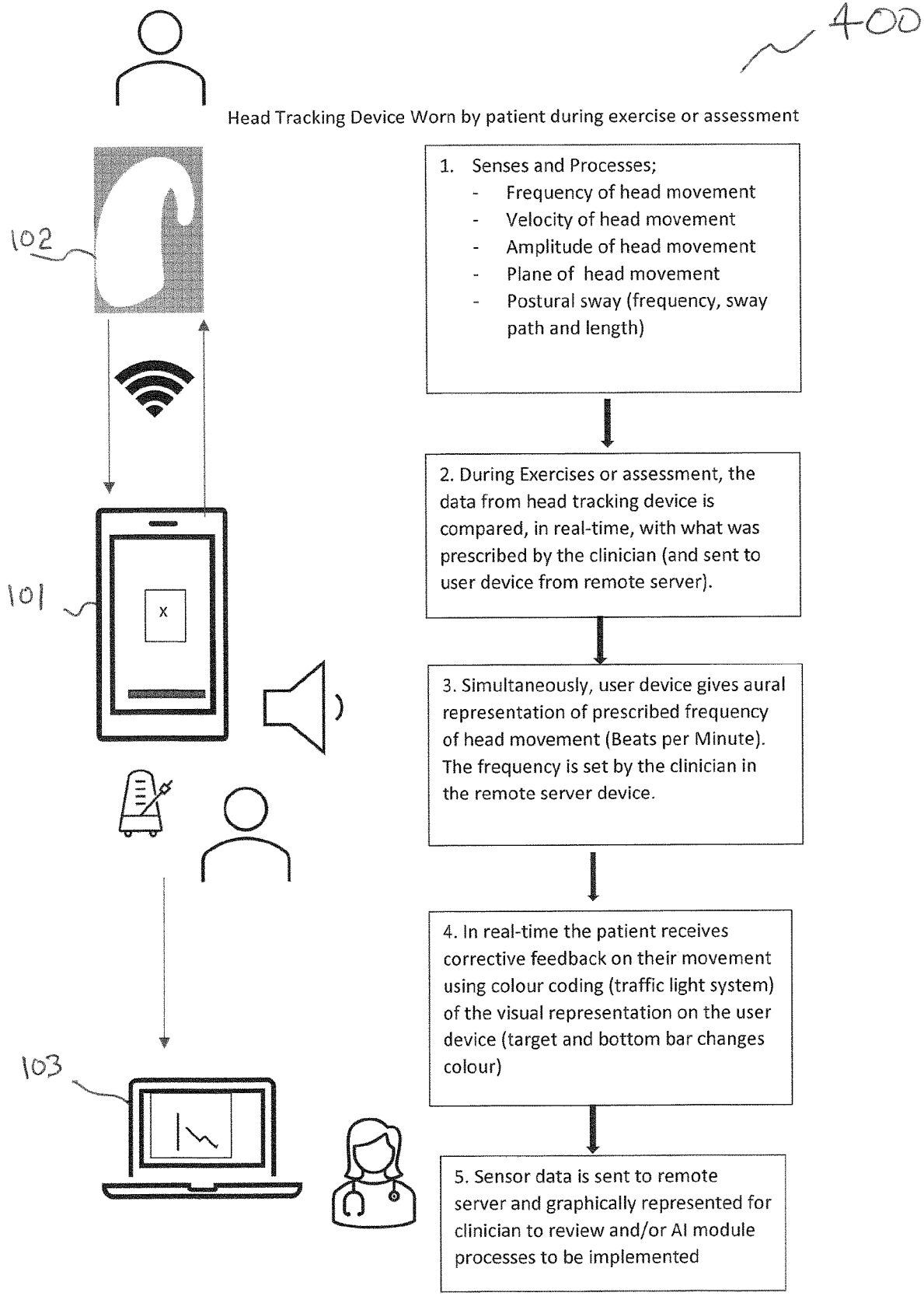
FIGS. 4 and 5 illustrates a number of detailed flow embodiments according to one or more aspects of the present invention.
Figure 5:
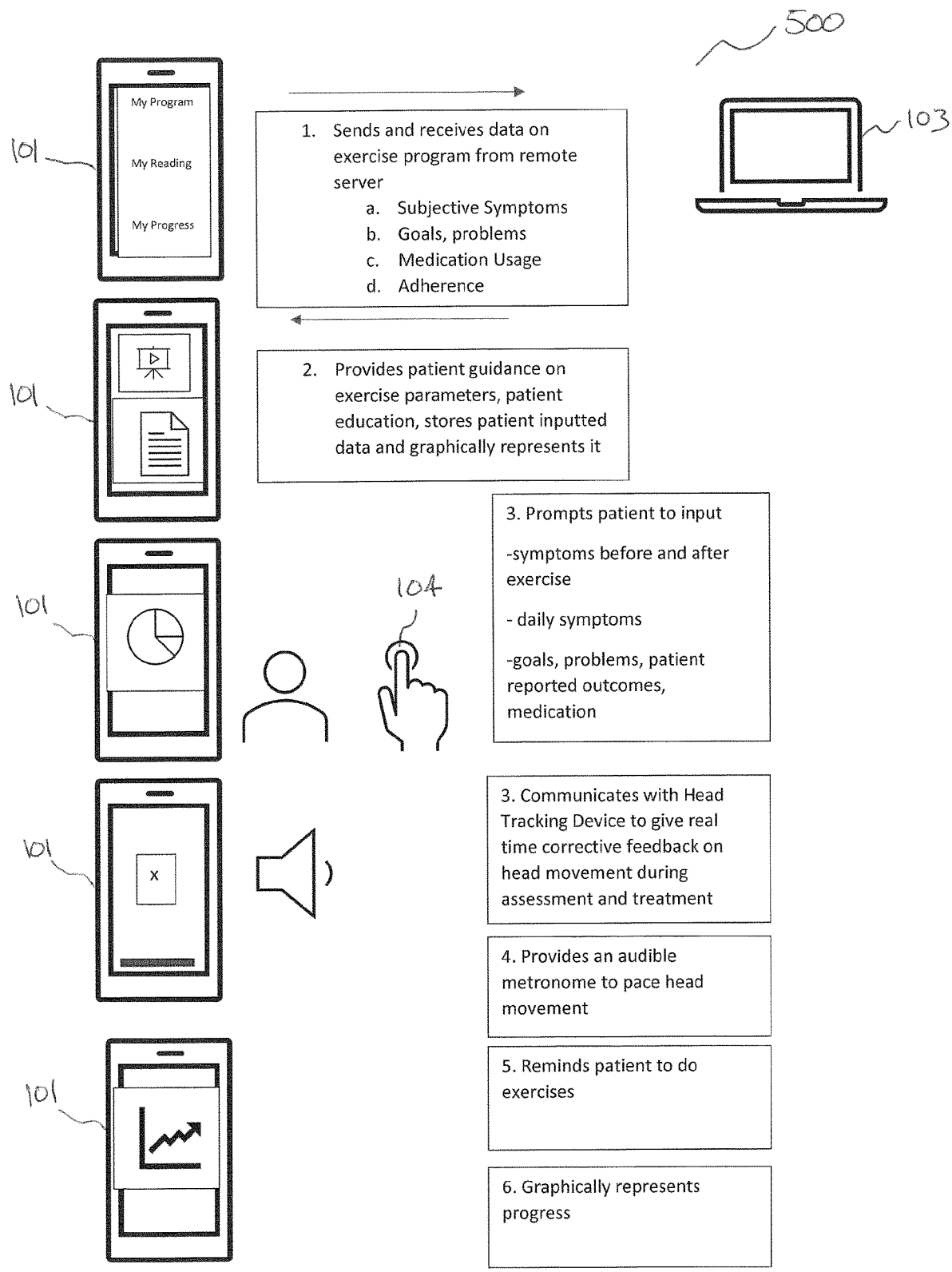

In the context of the present invention the system comprises at least one user device 101, a remote server device 103, and a head tracking device 102 and can be configured as per the flow paths illustrated in FIGS. 4 and 5, indicated generally by the reference numerals 400 and 500. In one embodiment of the invention the system can incorporate an optional artificial intelligence module configured to update the therapeutic configuration data. The flow path for enabling the invention is now described:

1. Server: Clinician deploys subjective assessments
2. User Device: Receives assessment material and prompts user to complete
   a. Symptoms & severity
   b. Self-denoted top problem
   c. Self-denoted treatment goals
   d. Self-denoted medication use
3. User device: Sends subjective assessment data to Server
4. Server: Processes the subjective data; sends appropriate information back to patient on symptoms, goals and other subjective parameters
5. Server: AI processing of data to calculate Falls Risk value, presentation severity and/or classification
6. Server: Clinician deploys physical assessment
7. User device and head tracking device: Physical Assessments undertaken by patient with clinician
8. User device: Prompts Patient to input symptoms following the physical assessment
9. Head tracking device: Transmits data to User Device
10. User Device: Sends all data to Server
11. Server: Clinician completes physical assessment
12. Server: Processes physical assessment data
13. Server: Combining subjective and physical assessment processed data, server AI processing to calculate patient falls risk profile, and outputs data with clinically meaningful descriptors
14. Server: Combining subjective and physical assessment processed data; sends a summary report to user device
15. Server: AI customised treatment plan is proposed to clinician
16. Server: Clinician prescribes a customised treatment, using symptoms and severity as a guide either as per proposed by system AI or, not as proposed by system AI.

In another embodiment of the invention the treatment cycle for a patient can be performed using the following steps:

1. Server: Clinician prescribes customised treatment, including therapeutic exercise and educational reading materials.
2. User Device: Receives personalised treatment prescribed
3. User device: User starts personalised program
4. User Device: Prompts patient to log current pre-program symptoms and/or Patient reported medication usage 5. User Device: Patient logs current symptoms and/or medication usage
6. User Device: May prompt patient to use head tracking device during therapy performance
7. User Device: User performs therapy exercises
8. Head tracking device: Transmits data to user device
9. User Device: Logs Head tracking data received and processes it
10. User Device & Head Tracking Device: Repeat steps 8 & 9 enabling real-time corrective feedback on performance parameters until exercise complete
11. User Device: Prompts patient to log current post-program symptoms
12. User device: Sends data to Server
13. Server: AI Processes combined data from head tracking device, recorded symptoms and medication adherence to calculate effect of exercises on symptoms in order to assess progress/prognosis/Fall Risk
14. Server: Presents data with clinically meaningful descriptors; sends summary data to user device
15. Server: Sends information on progress of treatment to user device
16. Server: AI Personally modified treatment plan for patient is proposed to clinician
17. Server: Clinician prescribes customised treatment, using symptoms as a guide either as per proposed by system AI or, not as proposed by system AI (loop back to step 1) and/or
18. Server: AI personally modified treatment plan is transmitted to user device or
19. Server: AI proposes patient discharge based on analysis of data, {symptoms reduction/plateau/resolution}

An advantage of the invention is that a clinician can, from the server portal, deploy and store outcomes, for example 1. physical objective Assessments 2. goals/problem recording, 3. subjective symptoms objectively recorded of patient problems/severity.

A further advantage of the invention is that the display can be on both the portal (server) and on the user device (phone app). The portal provides a display uniquely relating to Symptom change (classification—moderate, mild, severe) arising from exercise performance which is specific to a selected symptom, specific to a period of time/program, specific to an exercise performed at a given date.

It will be appreciated that the user interface on the user device also provides graphic display of data related to performance that is exercise specific, time specific, and uniquely frequency of movement specific (right movement, right frequency of head movement independent of body position). This information can also be displayed to a clinician or therapist at the remote server side. In the context of the present invention the terms clinician and therapist can be used interchangeably.

Although the present invention has been described with reference to specific embodiments, this description is not meant to be construed in a limiting sense. Various modifications of the disclosed embodiments, as well as alternate embodiments of the subject matter, will become apparent to persons skilled in the art upon reference to the description of the subject matter. It is therefore contemplated that such modifications can be made without departing from the spirit or scope of the present invention as defined.

Further, a person ordinarily skilled in the art will appreciate that the various illustrative method steps described in connection with the embodiments disclosed herein may be implemented using electronic hardware, or a combination of hardware and software. To clearly illustrate this interchangeability of hardware and a combination of hardware and software, various illustrations and steps have been described above, generally in terms of their functionality. Whether such functionality is implemented as hardware or a combination of hardware and software depends upon the design choice of a person ordinarily skilled in the art. Such skilled artisans may implement the described functionality in varying ways for each particular application, but such obvious design choices should not be interpreted as causing a departure from the scope of the present invention.

The method described in the present disclosure may be implemented using various means. For example, the system described in the present disclosure may be implemented in hardware, firmware, software, or any combination thereof. For a hardware implementation, the processing units, or processors(s) or controller(s) may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

For a firmware and/or software implementation, software code may be stored in the memory means and executed by a processor. The memory means may be implemented within the processor unit or external to the processor unit. As used herein the term "memory" refers to any type of volatile memory or non-volatile memory.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. a memory stick or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

What is claimed is:

1. A system for one or more of vestibular and balance rehabilitation, the system comprising:
   at least one user device comprising a data processor and network, and a display;
   at least one head tracking device configured to measure head motion data in real time and operably interfaced with the at least one user device, wherein the head motion data comprises one or more of amplitude, speed, and frequency of head motion; and
   a remote server device comprising a data processor, network and a server display, and operably interfaced with the at least one user device;

wherein the at least one user device is configured to
receive therapeutic configuration data from the remote server device representative of a clinical diagnosis specific to a user of the at least one user device;
output a user interface on the display;
generate visual stimuli and auditory stimuli in the user interface according to the therapeutic configuration data that is received during a training session, wherein the auditory stimuli comprises a metronome beat such that a frequency of the metronome beat is configured to be adjustable based on the therapeutic configuration data, wherein the frequency of the metronome beat is configured to be adjustable between training sessions based on real-time performance feedback, and is generated as one or more of frequency and velocity performed against what was prescribed and linked to symptom intensity;
receive the head motion data from the at least one head tracking device during the training session;
receive user inputted data pertaining to one or more symptoms of the user, wherein the user inputted data pertaining to said one or more symptoms of the user is selected from one or more of
user symptoms before the training session,
user symptoms during the training session,
user symptoms after the training session; and
generate real time sensory feedback in the user interface according to the head motion data that is received; and
generate visual feedback on the at least one user device based on the head motion data, wherein the visual feedback validates adherence of the user to prescribed exercises, and provides data points regarding difficulties or symptoms experienced by the user,
wherein the visual feedback and the head motion data that is measured and the user inputted data pertaining to the one or more symptoms of the user is communicated to the remote server device and a set of updated therapeutic configuration data is communicated to the at least one user device based on
the visual feedback,
the head motion data that is measured, and
the user inputted data pertaining to the one or more symptoms of the user.

2. The system as claimed in claim 1, wherein the at least one head tracking device comprises one or more of an accelerometer, a gyroscope, and a magnetometer.

3. The system as claimed in claim 1, wherein the head motion data is communicated to the remote server device by the at least one user device.

4. The system as claimed in claim 1, wherein the at least one user device is configured to receive the set of updated therapeutic configuration data from the remote server device.

5. The system as claimed in claim 1, wherein the at least one head tracking device is configured to be positioned behind an ear of the user.

6. A system for one or more of vestibular and balance rehabilitation, the system comprising:
at least one user device comprising a data processor, a network, and a display;
at least one head tracking device configured to measure head motion data in real time and operably interfaced with the at least one user device, wherein the head motion data comprises one or more of amplitude, speed, and frequency of head motion;

wherein the at least one user device is configured to
receive therapeutic configuration data representative of a clinical diagnosis specific to a user of the at least one user device;
output a user interface on the display;
generate a visual stimuli and auditory stimuli in the user interface according to the therapeutic configuration data that is received during a training session, wherein the auditory stimuli comprises a metronome beat such that a frequency of the metronome beat is configured to be adjustable based on the therapeutic configuration data;
receive the head motion data from the at least one head tracking device during the training session;
receive user inputted data pertaining to one or more symptoms of the user, wherein the user inputted data pertaining to the one or more symptoms of the user is selected from one or more of
user symptoms before the training session;
user symptoms during the training session;
user symptoms after the training session;
generate real-time sensory feedback in the user interface according to the head motion data that is received, wherein the real-time sensory feedback validates adherence of the user to prescribed exercises of the therapeutic configuration data, and further provides data points regarding difficulties or symptoms experienced by the user, including a metric of pain and rate of perceived exertion experienced by the user while performing exercises, and wherein the real-time sensory feedback provides a display uniquely relating to symptom change specific to a selected symptom, a period of time/program, and an exercise performed at a given date; and
process the head motion data and positional data and, the user inputted data pertaining to the one or more symptoms of the user and update a set of updated therapeutic configuration data to the at least one user device based on the head motion data and the positional data that is processed for use in a next training session, and wherein a remote server device is further configured to estimate patient falls risk profile based on the head motion data and the positional data that is processed, and
wherein the at least one head tracking device is further configured to provide feedback during postural stability retraining through parameters of postural sway including velocity, path length and amplitude.

7. The system as claimed in claim 6, wherein the at least one head tracking device comprises one or more of an accelerometer, a gyroscope, and a magnetometer.

8. The system as claimed in claim 6, wherein the at least one head tracking device is configured to be positioned behind an ear of the user.

9. A method for one or more of vestibular and balance rehabilitation, the method comprising:
providing at least one user device comprising a data processor and network, and a display;
providing at least one head tracking device;
providing a remote server device comprising a data processor, network and a server display, and operably interfaced with the at least one user device;
receiving a set of therapeutic configuration data from the remote server device, via the at least one user device, representative of clinical diagnosis of a user having vestibular or balance impairment;

outputting a user interface on the display:

generating and displaying a visual stimulus and auditory stimulus to the user via the user interface, wherein the visual stimulus based on the set of therapeutic configuration data, during a training session, wherein the auditory stimulus comprises a metronome beat such that a frequency of the metronome beat is configured to be adjustable based on the set of therapeutic configuration data,
- wherein the frequency of the metronome beat is configured to be adjustable between training sessions based on real-time performance feedback, and is generated as one or more of frequency and velocity performed against what was prescribed and linked to symptom intensity;

monitoring and measuring real time head motion data of the user in response to the visual stimulus and the auditory stimulus that is generated, wherein the real time head motion data comprises one or more of amplitude of head motion and speed of head motion and is measured via the at least one head tracking device;

receiving the real time head motion data from the at least one head tracking device during the training session;

generating real time visual and auditory feedback to the user according to the real time head motion data that is measured;

receiving user inputted data pertaining to one or more symptoms of the user, wherein the user inputted data pertaining to the one or more symptoms of the user is selected from one or more of
- user symptoms before the training session;
- user symptoms during the training session;
- user symptoms after the training session;

processing the real time head motion data and positional data and the user inputted data pertaining to the one or more symptoms of the user;

communicating the real time head motion data and positional data and the user inputted data to the remote server device; and updating the set of therapeutic configuration data and communicating the set of therapeutic configuration data to the at least one user device based on the real time head motion data and the positional data for use in a next training session.

10. The method as claimed in claim 9, further comprising generating an updated set of therapeutic configuration data based on the real time head motion data measured and the real time visual and auditory feedback.

* * * * *